United States Patent [19]

Vinegar et al.

[11] Patent Number: 4,866,983

[45] Date of Patent: Sep. 19, 1989

[54] ANALYTICAL METHODS AND APPARATUS FOR MEASURING THE OIL CONTENT OF SPONGE CORE

[75] Inventors: Harold J. Vinegar; Rocco DiFoggio; Pierre N. Tutunjian, all of Houston, Tex.

[73] Assignee: Shell Oil Company, Houston, Tex.

[21] Appl. No.: 181,762

[22] Filed: Apr. 14, 1988

[51] Int. Cl.$^4$ .............................................. E21B 49/08
[52] U.S. Cl. ..................................... 73/153; 250/301; 436/31
[58] Field of Search ...................... 73/151, 153, 155; 324/300, 303, 307, 312; 436/25, 30, 31; 250/301, 255, 339

[56] References Cited

U.S. PATENT DOCUMENTS

| | | | |
|---|---|---|---|
| 2,500,213 | 3/1950 | Stevens | 436/31 |
| 3,068,398 | 12/1962 | Shoolery et al. | 324/310 |
| 4,026,953 | 5/1977 | Pohl et al. | 568/884 |
| 4,164,653 | 8/1979 | Matumoto et al. | 250/301 |
| 4,265,860 | 5/1981 | Jennings et al. | 422/280 |
| 4,295,365 | 10/1981 | Meshri | 73/153 |
| 4,707,603 | 11/1987 | Miemelä et al. | 250/339 |

*Primary Examiner*—Stewart J. Levy
*Assistant Examiner*—Kevin D. O'Shea

[57] ABSTRACT

Methods and apparatus are disclosed for determining oil saturation in sponge coring using solvents which dissolve substantially all of the oil but none of the sponge. Two classes of such solvents are specified. One is aprotic, and the resultant concentration of oil in it is measured by proton NMR spectroscopy. The other has no C—H bonds, and the resultant concentration of oil in it is measured by infrared spectroscopy.

10 Claims, 5 Drawing Sheets

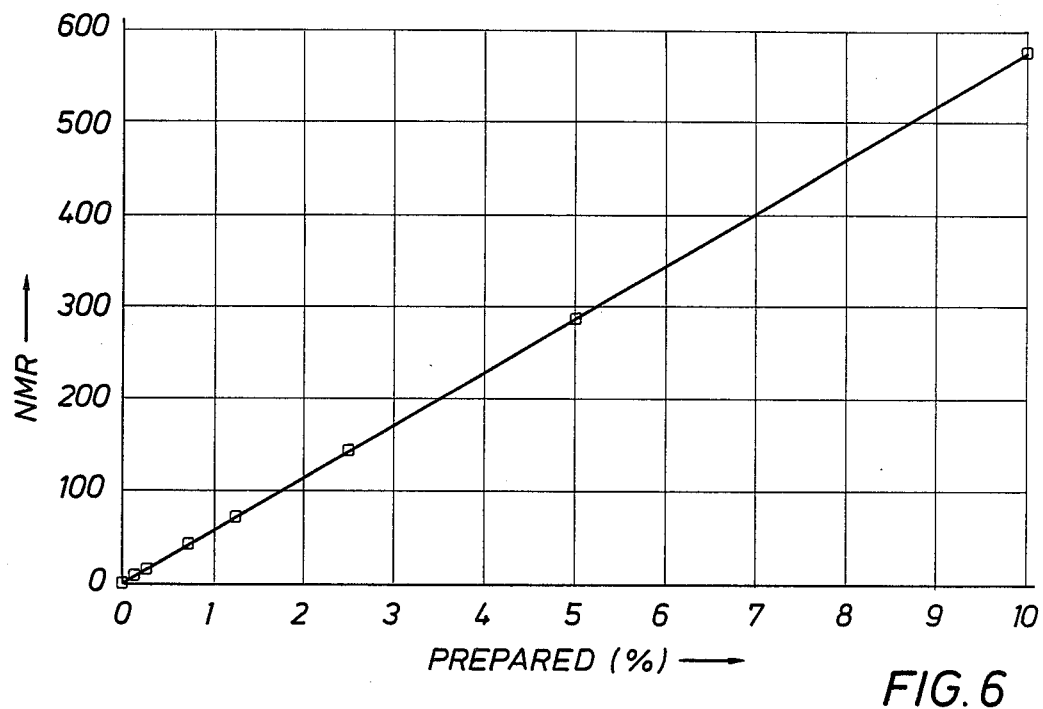
FIG. 6
FIG. 7
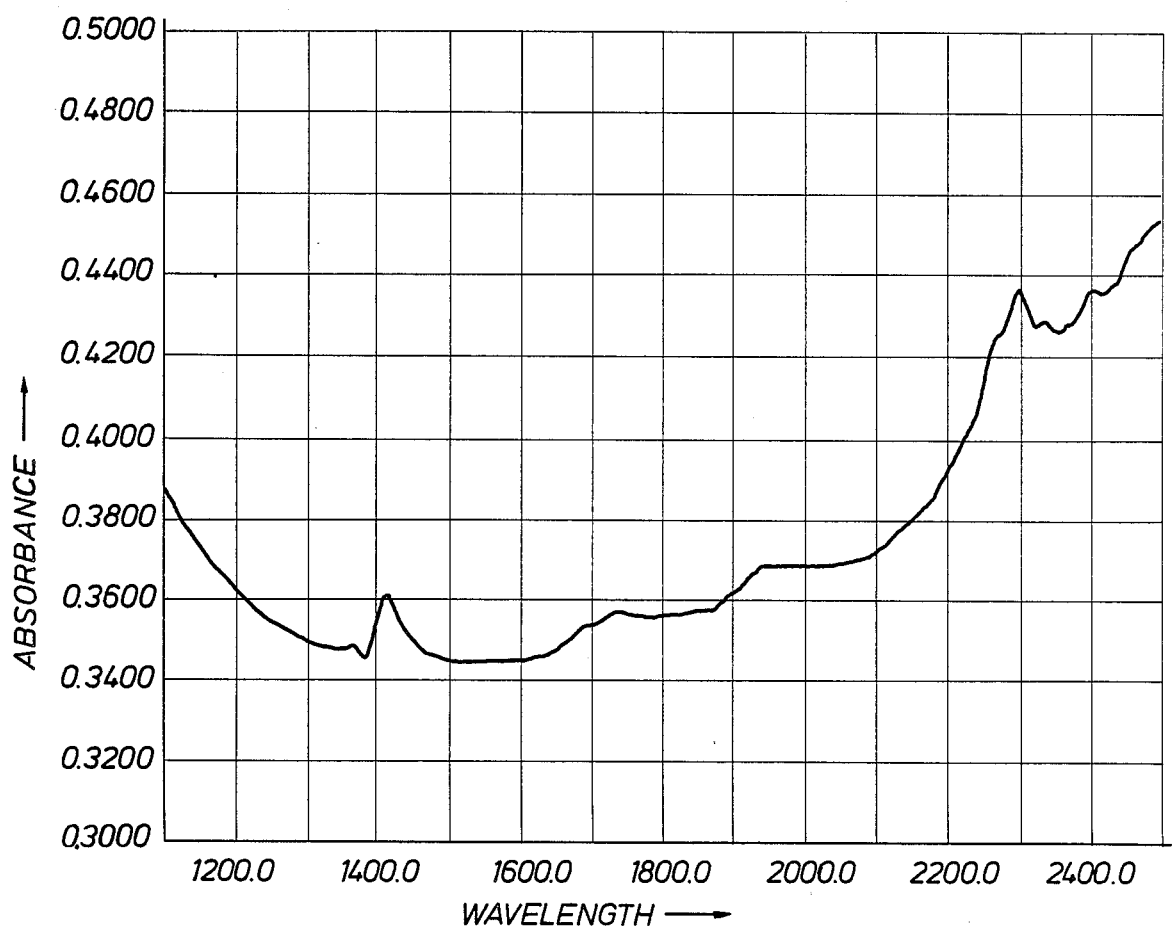

ANALYTICAL METHODS AND APPARATUS FOR MEASURING THE OIL CONTENT OF SPONGE CORE

CROSS-REFERENCE TO RELATED APPLICATIONS

Reference is made to prior U.S. patent application Ser. No. 122,622, filed Nov. 17, 1987 (originally U.S. patent application Ser. No. 814,334, filed Dec. 27, 1985), entitled "Method for Determining the Amount of Oil in a Sponge Core", now U.S. Pat. No. 4,787,983 the subject matter of which is expressly incorporated herein by reference.

Reference is also made to U.S. patent application Ser. Nos. 035,110, filed April 6, 1987, now U.S. Pat. No. 4,771,634, 035,111, filed April 6, 1987, now U.S. Pat. No. 478,566; 114,793, filed Oct. 28, 1987; 115,022, filed Oct. 28, 1987; 149,758, filed Jan. 29, 1988; and 164,153, filed Mar. 4, 1988.

BACKGROUND OF THE INVENTION

The present invention relates to the production of hydrocarbons from earth formations, and more specifically to a new method for determining the amount of oil in such earth formations.

The petroleum industry commonly relies on obtaining core from an earth formation to measure the amount of hydrocarbons contained in the formation. The three principal types of coring presently practiced are conventional core, pressure core, and sponge core. Conventional core is the least expensive means of coring, but fluids and gases present in the formation are displaced from the core as it is brought to the surface. These "blowdown" losses can be a significant fraction of the fluid contained in the core, and thus the oil saturation determined on conventional core will be too low.

Pressure core eliminates "blowdown losses" by maintaining the core at reservoir pressures until analyzed in the laboratory. However, pressure coring, which is no longer widely available as a commercial service, is quite expensive, typically ten times more expensive than conventional core. Moreover, core recovery from pressure coring operations tends to be lower than with conventional coring.

Recently, a third method of coring has been developed, called sponge coring. In this method, the "blowdown losses" from conventional core are trapped in an oil-wet polyurethane sponge lining on the inner barrel of a conventional core barrel. Sponge coring is substantially less expensive than pressure coring and often results in superior core recovery as well. Sponge coring has become the fastest growing section of the coring industry.

Once sponge core arrives in the laboratory, it is necessary to measure accurately the amount of hydrocarbons trapped in the polyurethane sponge. This has proven surprisingly difficult, as explained in greater detail in the above-noted '622 application. Various core laboratories have tried mechanical and pressurized solvent methods for extracting the sponge, but none has yielded an accurate or precise method for determining the oil volumes.

The above-mentioned patent '622 application describes a method for extracting oil from a polyurethane sponge without substantially affecting the sponge by using a low boiling point solvent selected from among the class of cycloalkanes, ethers, and Freons. With these low boiling point solvents, the solvent can simply be evaporated away after extraction. Alternatively, the patent application discloses that a test solution of oil removed from the sponge can then be compared with a standard solution using near infrared (IR) spectroscopy or supercritical fluid chromatography. Near IR spectroscopy measures the number of C—H bonds in the sample, while supercritical fluid chromatography measures the aromatic concentration in the solution. Among the solvents specifically disclosed in that patent application are the cycloalkanes: cyclobutane, cyclopentane, cyclohexane; the ether; diethyl ether; and the Freons: Freon-11, and Freon-114.

The new methods thus described in the above-noted patent applications have significant advantages over past technologies. Nevertheless, it has been found that, although the above-mentioned solvents do not substantially dissolve the sponge, there are nonetheless some unpolymerized polyurethane precursors that are extracted by these solvents. Polyurethane is made by polymerization of a diisocyanate and a diol. These chemical structures have been identified in significant quantity (compared to the dissolved oil) by $^1$H and $^{13}$C nuclear magnetic resonance studies of extracts using the Freon-11 solvent of the above-mentioned method. This necessitates, in the presence of the dissolved polyurethane components, several additional stages of distillation, centrifugation, and emulsion breaking to practice the step of evaporating the solvent from the oil. Moreover, the separation between the extracted sponge layer and the oil/solvent is, even then, not always clear, particularly at low oil concentration. This can lead to errors in volumetric determination of the oil content.

A need therefore remains for a new and improved method and apparatus for use in determining the oil saturation of an earth formation by means of sponge coring, which method and apparatus are not subject to the several limitations discussed above. More particularly, a need remains for a method and apparatus for performing such analyses which can readily accommodate and account for these small amounts of dissolved unpolymerized polyurethane precursors in the oil/solvent mixture, essentially regardless of concentration. A need also remains for such a method and apparatus which can preferably perform the required analysis quickly and accurately, ideally without the time-consuming need to evaporate part of the solvent and/or to separate out the dissolved unpolymerized polyurethane precursors. The method and apparatus should also be uncomplicated, versatile, and reliable, inexpensive to implement and perform, and readily suited to the widest possible utilization in determining oil saturations of earth formations by means of sponge coring.

SUMMARY OF THE INVENTION

Briefly, the present invention meets the above needs and purposes with new, improved, and superior methods and apparatus for sponge analysis having particularly high accuracy, repeatability, and speed of analysis. In the preferred embodiment, the sponge is first extracted using a selected solvent which is a good solvent for the oil, is "aprotic", i.e., has no protons ($^1$H nuclei) in its molecular structure, and which does not substantially affect the sponge. As an alternative, the solvent may have no C—H bonds. The use of aprotic solvents enables $^1$H NMR spectroscopy to be used to determine the oil content in the extract. The use of a solvent with no C—H bonds enables IR spectroscopy to be used. NMR spectroscopy is preferred because the polyurethane signal can be accurately distinguished from the oil signal on the basis of its chemical shift spectra and thus spectrally subtracted, as described hereinbelow. In IR spectroscopy various absorbance peaks in the IR spectrum of polyurethane can similarly be used to distinguish it from the oil signal.

The aprotic solvent is selected to be a good solvent for the oil yet leave the sponge substantially unaffected. As an initial screening procedure, the solvent is selected to have a Hansen solubility parameter significantly different from that of polyurethane. The Hansen solubility parameter is an extension of the Hildebrandt solubility parameter to cases where there are polar interactions and hydrogen bonding. The solubility of polyurethane in various solvents has been studied by A. Chapiro, M. Lamothe, and T. Le Doan, "Parametre de Solubilite D'un Polyurethanne de Structure Definie", European Polymer Journal, Vol. 14, pp. 647–650, (1978). (Note that in that paper the Hansen solubility parameter scale is one-half that utilized in the U.S. literature). They concluded the Hansen solubility parameter for their polyurethane was 19.2. A solvent with a Hansen solubility parameter in this range will dissolve the polyurethane. Hence the solvent is selected to be outside this range. Typically the further the solvent's Hansen parameter is removed on either side from this range the less the polyurethane solubility.

The Hansen solubility parameters for a variety of solvents are tabulated by A. Barton, "Handbook of Solubility Parameters and Other Cohesion Parameters", CRC Press, Boca Raton, Florida, 1983. All the preferred solvents mentioned in the '622 patent application (above) have values below polyurethane, e.g. 16.7 for cyclohexane, 14.5 for diethyl ether, 15.5 for Freon-11, and 12.8 for Freon-114. However, all of these solvents were also selected for their low boiling points. In the present invention the boiling point of the solvent need not be low, which enables use of a much larger number of solvents. The preferred solvents may now be Freon-113 (trichlorotrifluoroethane, commercial trademark Freon-TF), b.p.= 47.6° C, Hansen solubility parameter=14.9; Freon-112 (tetrachlorodifluoroethane), b.p.=92.8° C, Hansen solubility parameter=16.0; and tetrachloroethylene, b.p.=121° C, Hansen solubility parameter=20.3. Because these boiling point are well above room temperature, the extraction vessels can be simplified (e.g., special cooling for a Soxhlet extraction unit's low temperature condenser is not required). Note that tetrachloroethylene is the first solvent disclosed whose Hansen solubility parameter lies above that of polyurethane. It should be noted, however, that the Hansen solubility parameter should be used only as a first pass for selecting the solvent, and that each solvent should be experimentally tried on a section of polyurethane sponge.

In particular, tetrachloroethylene has been found to be an excellent solvent for crude oil, unlike Freon-11 which does not dissolve above one-fourth of the asphaltene components of crude oils. With Freon-11, therefore, the extraction time is longer and some fraction of the crude oil may not be counted. Tetrachloroethylene, in addition to being an excellent solvent for crude oils, has low toxicity. As with many of the halogenated hydrocarbons, it also has low dissolving power for polyurethane sponge.

A perdeuterated solvent could also be used in the practice of this invention. However, deuterated solvents are substantially more expensive than the halogenated hydrocarbons listed above.

Once the oil has been extracted from the sponge, various properties of the oil may be determined by NMR on the extract, such properties including, for example, aliphatic/aromatic ratio, oil viscosity, oil diffusion coefficient, and so forth. These are described in the above-noted co-pending '022 patent application.

It is therefore an object of the present invention to provide a new and improved method and apparatus for use in determining the oil saturation of an earth formation by means of sponge coring; such a method and apparatus in which substantially all of the oil and substantially none of the sponge in a sponge core sample are dissolved into a solvent selected from the class consisting of solvents having no protons in their structure and solvents having no C—H bonds in their structure; in which the resultant oil concentration in the solvent is then measured; in which the measurement is preferably by proton NMR spectroscopy when the selected solvent is aprotic; in which such an aprotic solvent may be deuterated or perdeuterated; in which the measurement is preferably by infrared spectroscopy when the selected solvent has no C—H bonds in its structure; in which the solvent may be a fully halogenated aromatic; in which the solvent may be a fully halogenated hydrocarbon; in which the measurement may be made by subtracting the spectrum of the extracted polyurethane from the total measured spectrum to determine the oil concentration; and to accomplish the above objects and purposes in an inexpensive, uncomplicated, versatile, and reliable method and apparatus, inexpensive to implement and perform, and readily suited to the widest possible utilization in determining oil saturations of earth formations by sponge coring.

These and other objects and advantages of the invention will be apparent from the following description, the accompanying drawings, and the appended claims.

BRIEF DESCRIPTION OF THE DRAWINGS

FIG. 6 shows the $^1$H NMR-determined oil content on a set of reference samples of crude oil mixed with Freon-11;

FIG. 7 shows the IR spectrum of a Freon-11 extract of a clean polyurethane sponge;

DESCRIPTION OF THE PREFERRED EMBODIMENT

Figure 1:
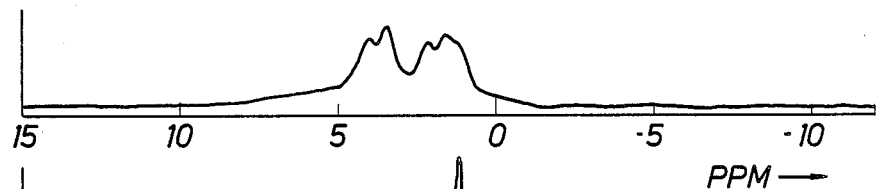
FIG. 1 shows the $^1$H NMR spectrum of a Freon-11 extract of clean polyurethane sponge.

With reference to the drawings, the new and improved analytical methods for measuring the oil content of sponge core, and the apparatus therefor according to the present invention, will be described. FIG. 1 shows a $^1H$ NMR spectrum of a Freon-11 extract of a clean polyurethane sponge (containing no crude oil). The four peaks are consistent with low molecular weight polyurethane and the polyurethane precursors extracted from the sponge. The measurements were made on a General Electric CSI-2T at 85 MHz using a 250 cc fluid sample in a glass bottle. The background signal from the NMR probe, sample bottle, and Freon-11 were previously subtracted.

Figure 2:
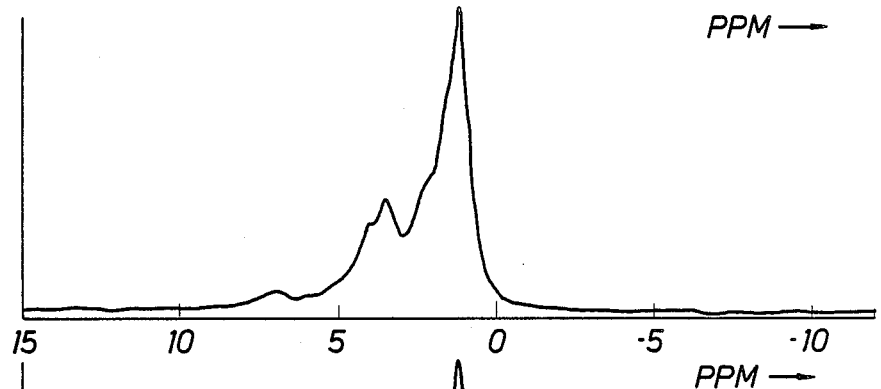
FIG. 2 shows the $^1$H NMR spectrum of a Freon-11 extract of a polyurethane sponge containing crude oil.

In FIG. 2 there is shown the $^1H$ NMR spectrum of a Freon-11 extract of a polyurethane sponge containing crude oil. There is now, in addition to the polyurethane peaks, the aliphatic and aromatic oil peaks at 1.2 ppm and 7.2 ppm chemical shift. Note that in this example the signal from the polyurethane is about equal to that from the oil. However, the actual amount of residual polyurethane precursors is highly variable from sample to sample. Thus, the Freon-11 can extract a significant quantity of polyurethane precursors from the sponge compared to the oil present in the sponge. Also note that some of the polyurethane signal lies superimposed on the aliphatic oil signal. As above, the background signal from the NMR probe, sample bottle, and Freon-11 were previously subtracted.

Figure 3:
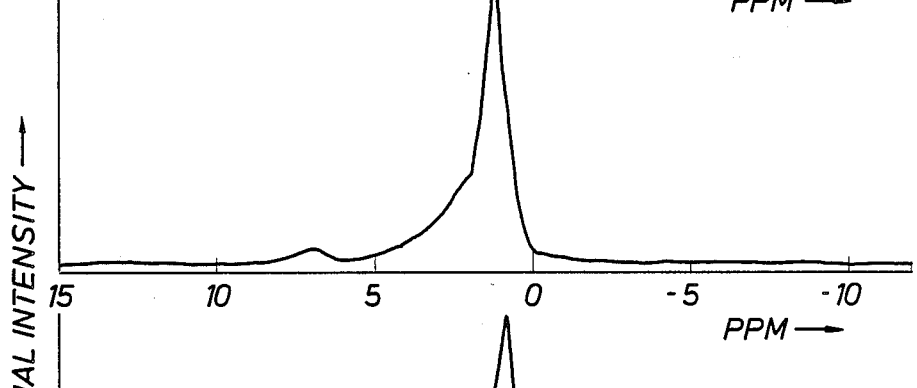
FIG. 3 shows the $^1$H NMR spectrum of the crude oil used in FIG. 2.

Referring now to FIG. 3, there is shown the $^1H$ NMR spectrum of the crude oil used in FIG. 2. The background signal from the NMR probe, sample bottle, and Freon-11 were previously subtracted.

Figure 4:
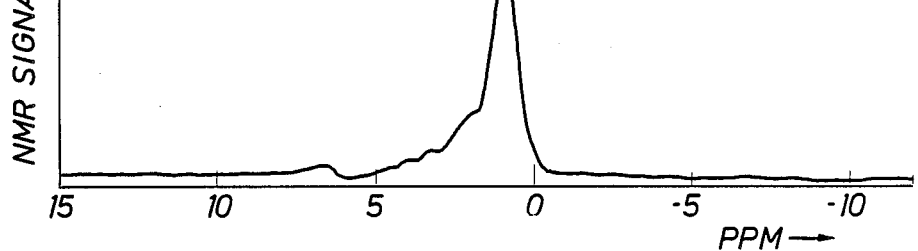
FIG. 4 shows the spectral subtraction of the $^1$H NMR polyurethane sponge signal from the $^1$H NMR Freon-11 crude extract signal.

Referring now to FIG. 4, there is shown the spectral subtraction of the $^1H$ NMR polyurethane sponge signal (FIG. 1) from the $^1H$ NMR Freon-11 crude extract signal (FIG. 2). The spectral subtraction is done on the General Electric CSI-2T, using the spectrum from FIG. 1. This spectrum is multiplied by a variable amount Q, and subtracted from FIG. 2. The variable Q is adjusted until the polyurethane peaks are minimized in the subtracted spectrum (FIG. 4). Note that FIG. 4 now looks very similar to FIG. 3, which is the spectrum of the crude oil alone. Even though some of the polyurethane signal lay underneath the aliphatic oil signal, the spectral subtraction succeeds because the polyurethane signal that is resolved from the aliphatic oil signal bears a substantially fixed relationship to the polyurethane signal which lay underneath the aliphatic oil signal. Thus, by basing the subtraction on the polyurethane signal which is resolved, the signal underlying the aliphatic peak is also subtracted correctly.

Figure 5:
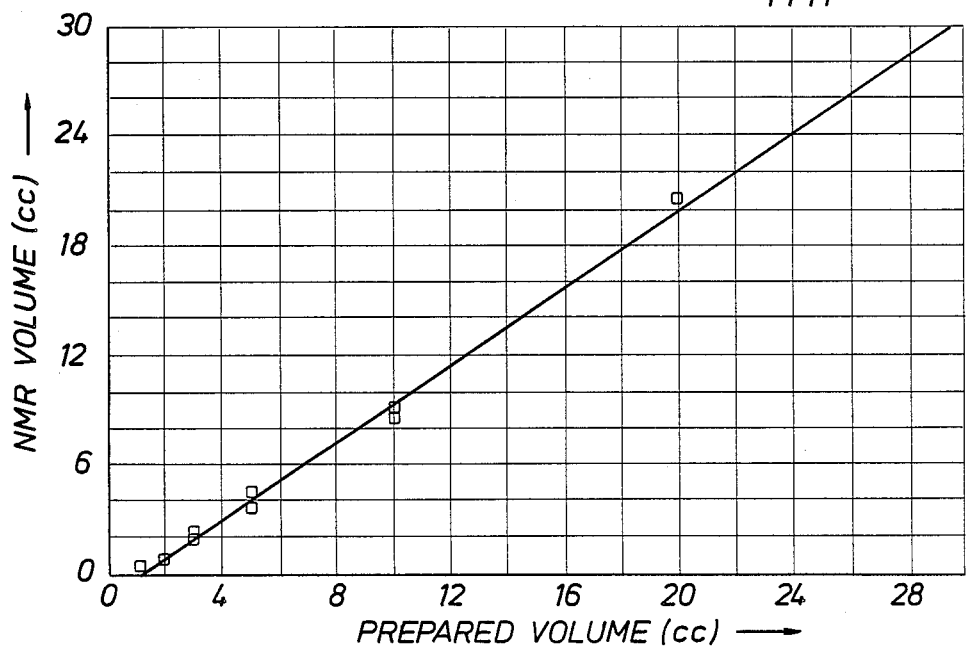
FIG. 5 shows the $^1$H NMR-determined oil content of the Freon-11 extracts of a suite of oil-spiked polyurethane sponges as compared with the prepared oil content.

Referring now to FIG. 5, there is shown the $^1H$ NMR-determined oil content of a suite of polyurethane sponges compared with the prepared oil content in that suite. The oil content is determined from the spectra by integrating the signal under the aliphatic and aromatic peaks of the spectrum, and ratioing this signal to that from a known reference quantity of oil. The excellent agreement demonstrates the accuracy, precision, and repeatability of this invention. Note that the reference oil need not be the same crude as in the sponge, because the aliphatic proton density of crude oils is substantially the same, namely 0.111 moles/cc at 25° C.

Referring now to FIG. 6, there is shown the results of NMR spectroscopy on 250 cc bottles of Freon-11 mixed with known amounts of West Texas Intermediate crude. The standard error of NMR measurement is less than 0.2% for the samples and the correlation coefficient is 0.999999.

In addition to proton NMR, the oil content may also be determined by $^{13}C$ NMR spectroscopy. This has the advantage of allowing solvents to be used whose carbon spectrum is well-resolved from the aliphatic and aromatic oil spectrum. However, the disadvantage of $^{13}C$ spectroscopy is low signal-to-noise, requiring several hours per analysis as compared to several minutes for proton NMR.

Referring now to FIG. 7, there is shown an IR spectrum of a Freon-11 extract of a clean (oil-free) polyurethane sponge. Various absorbance peaks are observed, including those at 1730 nm, 1910 nm, 2140 nm, and 2300-2400 nm. The measurements were made on a Near IR spectrometer using a 0.5 mm sample cup.

Figure 8:
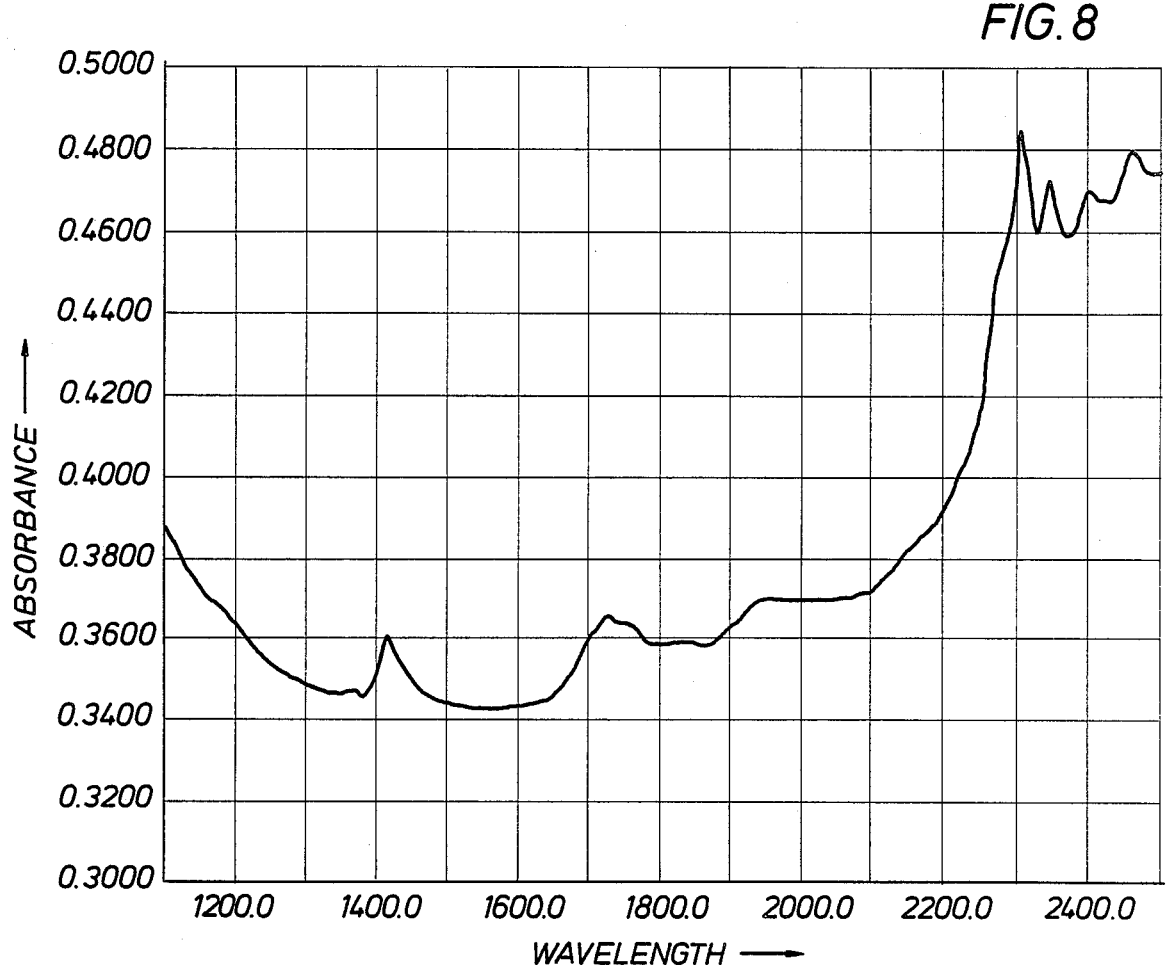
FIG. 8 shows the IR spectrum of a Freon-11 extract of a polyurethane sponge containing crude oil.

Referring now to FIG. 8, there is shown the IR spectrum of a Freon-11 extract of a polyurethane sponge containing crude oil. The aliphatic oil peaks at 1730 nm and 2300 nm–2400 nm superimpose on two of the polyurethane peaks. However, the two polyurethane peaks at 1910 nm and 2140 nm do not occur in the spectra of the oil.

Figure 9:
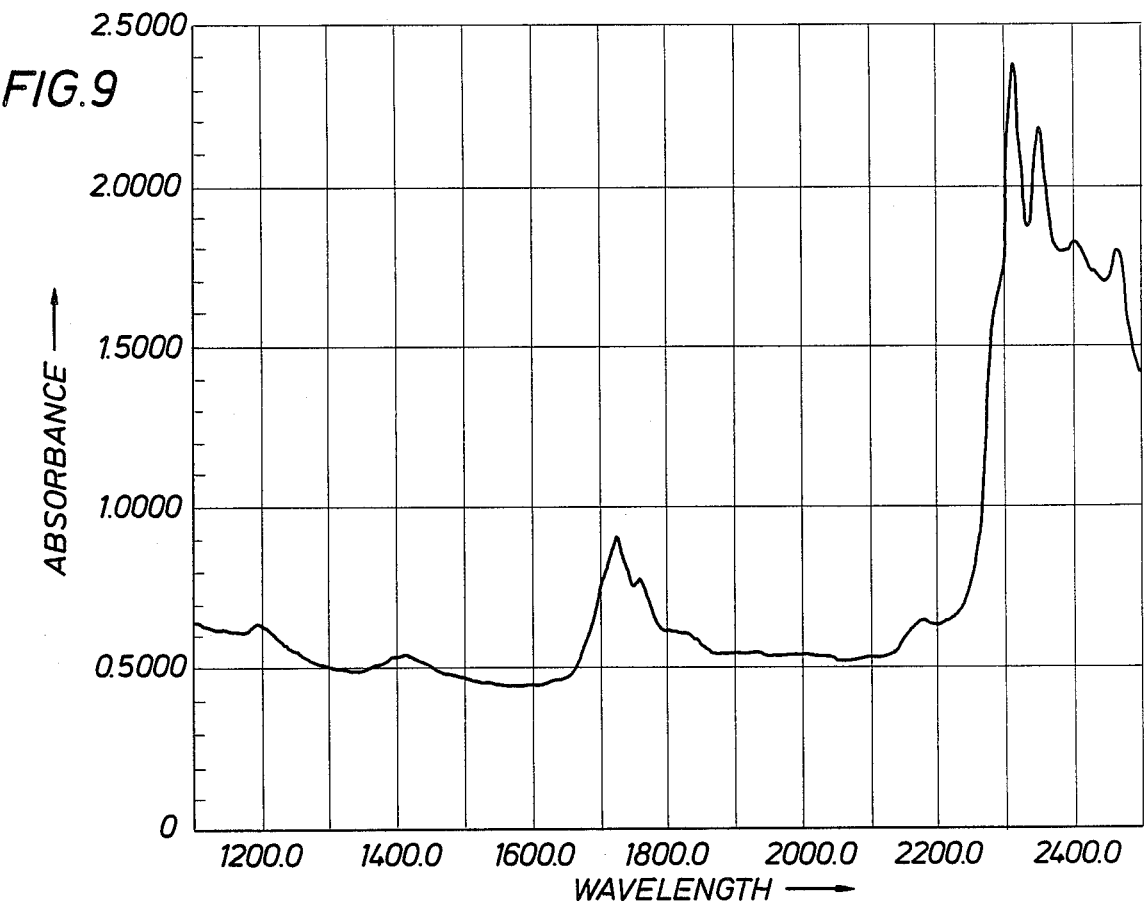
FIG. 9 shows the IR spectrum of the crude oil used in FIG. 7.

Referring now to FIG. 9, there is shown the IR spectrum of the crude oil used in FIG. 8.

Figure 10:
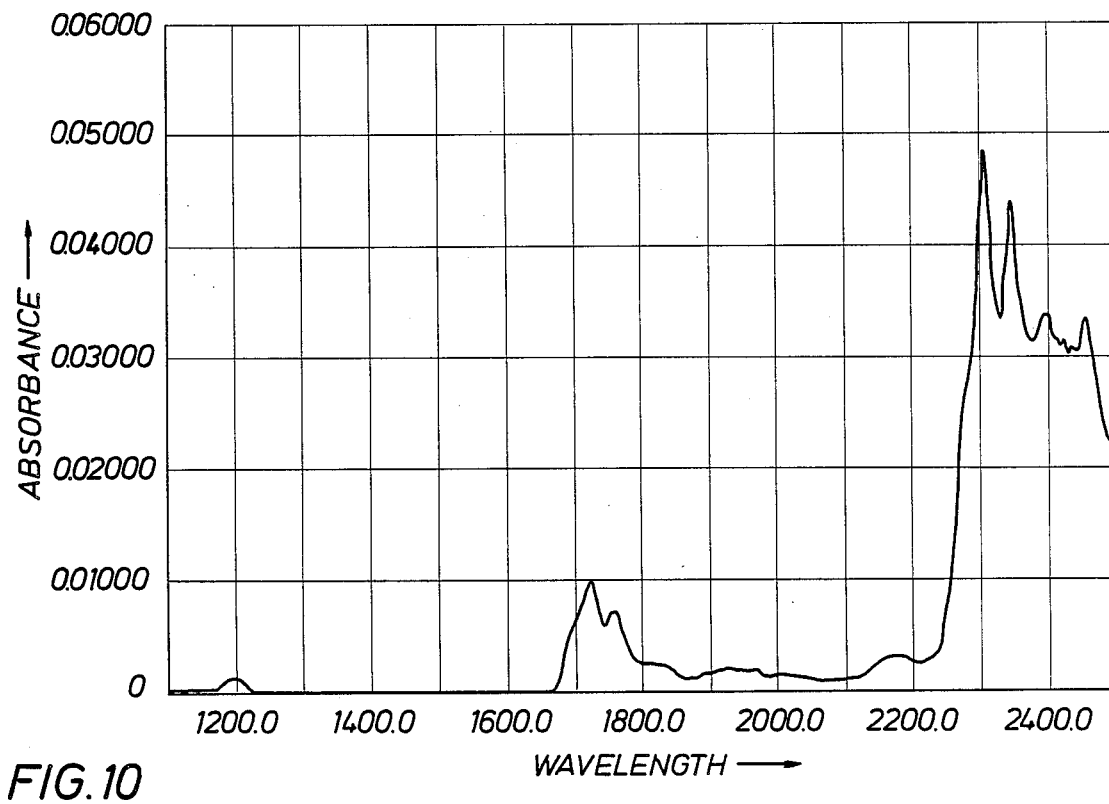
FIG. 10 shows the spectral subtraction of the IR signal from the polyurethane from the IR Freon-11 crude extract signal.

Referring now to FIG. 10, there is shown the spectral subtraction of the IR polyurethane sponge signal (FIG. 7) from the IR polyurethane plus crude oil extract signal (FIG. 8). The amount subtracted is adjusted until the two polyurethane peaks at 1910 nm and 2140 nm are minimized in the subtracted spectrum, FIG. 10. Note that FIG. 10 now looks similar to FIG. 9, which is the spectrum of the crude oil alone. Even though some of the polyurethane signal lay underneath the aliphatic oil signal, the spectral subtraction succeeds because the polyurethane signal that is resolved from the aliphatic oil signal bears a substantially fixed relationship to the polyurethane signal which lay underneath the aliphatic oil signal. Thus, by basing the subtraction on the polyurethane signal which is resolved, the signal underlying the aliphatic peak is also subtracted correctly.

Figure 11:
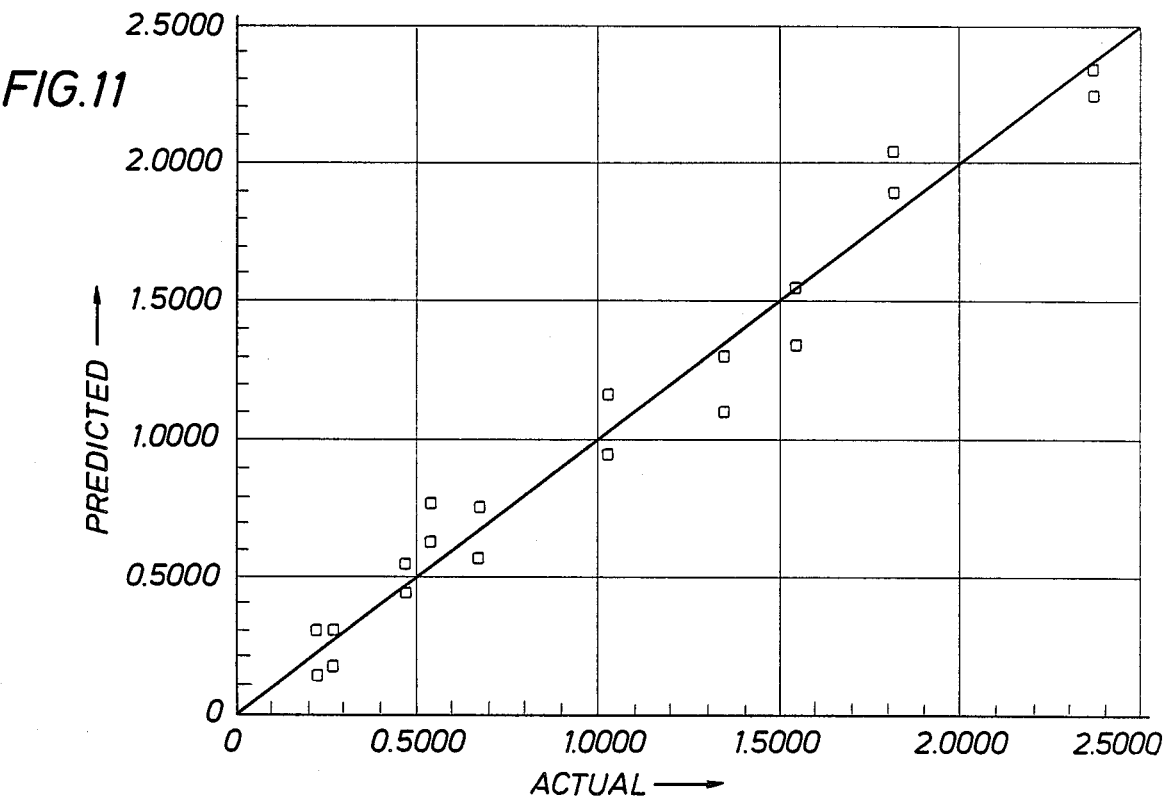
FIG. 11 shows the IR-determined oil content on a set of reference samples of crude oil mixed with Freon-11.

Referring now to FIG. 11, there is shown the results of IR spectroscopy on Freon-11 mixed with known amounts of crude. The estimated prediction error is 0.145% of solution concentration.

Figure 12:
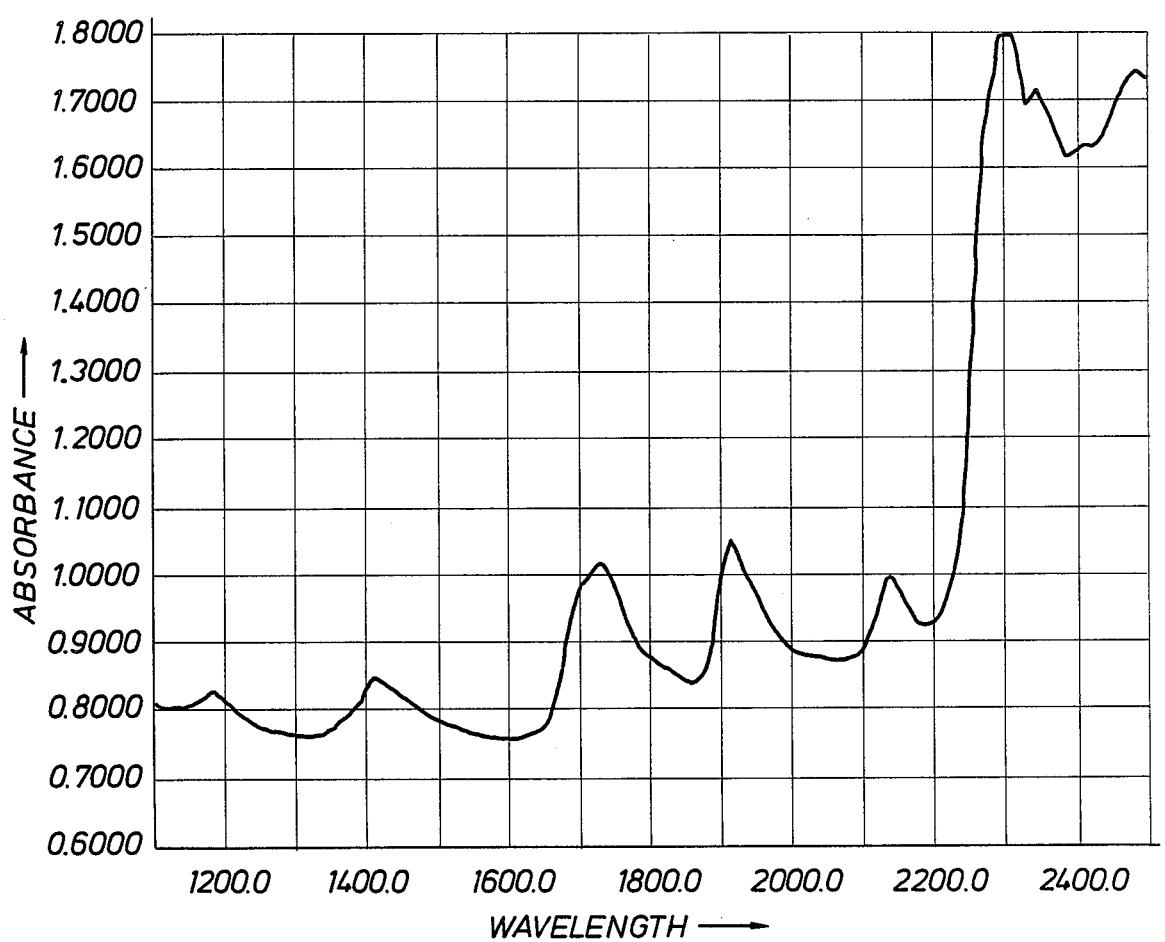
FIG. 12 shows an extract like that in FIG. 7 but which has been concentrated by evaporation of most of the solvent.

Referring now to FIG. 12, there is shown, for illustrative purposes, a Freon-11 extract of clean polyurethane sponge which has been concentrated by evaporation of most of the Freon-11 solvent. The peaks at 1730 nm, 1910 nm, 2140 nm, and 2300-2400 nm are readily apparent.

As may be seen, therefore, the present invention has numerous advantages. Principally, it provides a substantially improved sponge coring method and apparatus which are not subject to the several limitations discussed earlier. The invention easily accommodates and accounts for small amounts of dissolved unpolymerized polyurethane precursors in the oil/solvent mixture, essentially regardless of the concentration. It performs the analysis quickly and accurately, and without the time-consuming need to evaporate part of the solvent and/or to separate out the dissolved unpolymerized polyurethane precursors.

While the IR examples employed near-infrared spectroscopy, regular infrared spectroscopy will work as well. The strong characteristic group frequency for crude oils in infrared spectroscopy are at 1450 cm$^{-1}$ (6.9$\mu$) and 2950 cm$^{-1}$ (3.45$\mu$) for the alkane groups and 700–850 cm$^{-1}$ (14.4$\mu$–11.9$\mu$) for the aromatic groups.

The invention has great utility for extraction on a PVC-lined polyurethane sponge as well as aluminum-lined polyurethane sponge. In this case the Freon solvent may also remove some of the PVC plasticizer, which is usually dioctyl phthalate. Dioctyl phthalate contributes both alkane groups and aromatic groups which overlap with the crude spectrum, but has a distinctive infrared feature from the carboxyl group (O=C—O), namely a very strong line at 1700–1750 cm$^{-1}$ (5.9$\mu$–5.7$\mu$) which can be used for subtracting the plasticizer spectrum.

As a variation on the solvents, although more expensive, a deuterated solvent can be used with the NMR spectroscopy, for example, by first measuring the response of the solvent to determine the proportions of hydrogen and deuterium therein. Then, along the same principles discussed above, the oil/solvent extract mixture is analyzed by NMR spectroscopy for the total hydrogen response and also for the total deuterium response. Then, using the deuterium response, the portion of the hydrogen response caused by the solvent is easily determined based upon the proportions just determined above, and subtracted from the mixture's hydrogen signal. The result is the portion due to the dissolved crude oil.

When a perdeuterated (nearly 100% deuterated) solvent is utilized, the technique is even simpler since the solvent contributes essentially zero hydrogen signal, so none needs to be subtracted.

The method and apparatus of the present invention are thus uncomplicated, versatile, and reliable, inexpensive to implement and perform, and readily suited to the widest possible utilization in determining oil saturations of earth formations by means of sponge coring.

Therefore, while the methods and forms of apparatus herein described constitute preferred embodiments of this invention, it is to be understood that the invention is not limited to these precise methods and forms of apparatus, and that changes may be made therein without departing from the scope of the invention.

What is claimed is:

1. A method for use in determining the oil saturation of an earth formation by means of sponge coring, using polyurethane sponge, comprising:
   (a) dissolving substantially all of the oil and substantially none of the sponge, in a sponge core sample, into a solvent having a Hansen solubility parameter of different than that of the sponge and selected from the class consisting of:
   (i) solvents having no protons in their structure,
   (ii) deuterated solvents, and
   (iii) solvents having no C—H bonds in their structure,
   (b) extracting the solvent and solutes from the core sample, and
   (c) measuring the resultant oil concentration in the solvent and solutes extracted from the core sample.

2. The method of claim 1 wherein the selected solvent has no protons in its structure and said measuring step further comprises measuring the oil concentration by obtaining the $^1$H NMR spectrum of the solvent and solutes extracted from the core.

3. The method of claim 2 wherein the solvent is a fully halogenated aromatic.

4. The method of claim 2 wherein the solvent is a fully halogenated hydrocarbon.

5. The method of claim 2 wherein said measuring step further comprises obtaining a solvent and solute extract of a clean polyurethane sponge and measuring the $^1$H NMR spectrum of the solvent and solute extract of the clean sponge, adjusting the magnitude of one peak of the spectrum that does not overlap the oil structure in the $^1$H NMR spectrum of the solvent and solutes extracted from the core sample to equal the corresponding peak in the $^1$H NMR spectrum of the solvent and solutes extracted from the core, subtracting the adjusted $^1$H NMR spectrum of the solvent and solute extracted from the clean sponge from the $^1$H NMR spectrum of the solvent and solutes extracted from the core to determine the oil concentration.

6. The method of claim 1 wherein the selected solvent is predeuterated and said measuring step further comprises measuring the oil concentration in the solvent and solutes extracted from the core by $^1$H NMR spectroscopy.

7. The method of claim 1 wherein the selected solvent has no C—H bonds in its structure and said measuring step further comprises measuring the oil concentration in the solvent and solutes by infrared spectroscopy.

8. The method of claim 7 wherein the solvent is a fully halogenated aromatic.

9. The method of claim 7 wherein the solvent is a fully halogenated hydrocarbon.

10. The method of claim 7 wherein said measuring step further comprises obtaining a solvent and solute extract from a clean polyurethane sponge;
   measuring the IR spectrum of the solvent and solute extracted from the clean polyurethane sponge and adjusting the peaks of this spectrum to equal similar peaks in the IR spectrum of the solvent and solutes extracted from the core sample; and
   subtracting the adjusted IR spectrum from the total IR spectrum of the core.

* * * * *